US012797440B2

(12) United States Patent
Peesay et al.

(10) Patent No.: US 12,797,440 B2
(45) Date of Patent: Nov. 17, 2026

(54) SILK FIBROIN-CONTAINING COMPOSITION AND METHODS OF USE THEREOF

(71) Applicant: Georgetown University, Washington, DC (US)

(72) Inventors: Morarji Peesay, Germantown, MD (US); Makarand Paranjape, Ashton, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 18/664,616

(22) Filed: May 15, 2024

(65) Prior Publication Data

US 2024/0408173 A1 Dec. 12, 2024

Related U.S. Application Data

(63) Continuation of application No. 16/757,195, filed as application No. PCT/US2018/056608 on Oct. 19, 2018, now abandoned.

(60) Provisional application No. 62/574,993, filed on Oct. 20, 2017.

(51) Int. Cl.

| | |
|---|---|
| ***A61K 47/06*** | (2006.01) |
| ***A61K 9/00*** | (2006.01) |
| ***A61K 31/02*** | (2006.01) |
| ***A61K 38/17*** | (2006.01) |
| ***A61P 11/00*** | (2006.01) |

(52) U.S. Cl.

CPC ........ *A61K 38/1767* (2013.01); *A61K 9/0082* (2013.01); *A61K 31/02* (2013.01); *A61P 11/00* (2018.01)

(58) Field of Classification Search

None

See application file for complete search history.

(56) References Cited

U.S. PATENT DOCUMENTS

| | | | |
|---|---|---|---|
| 5,245,012 | A | 9/1993 | Lombari et al. |
| 5,770,585 | A | 6/1998 | Kaufman et al. |
| 7,635,755 | B2 | 12/2009 | Kaplan et al. |
| 2006/0034945 | A1 | 2/2006 | Nishimura et al. |
| 2009/0214649 | A1 | 8/2009 | Gazit et al. |
| 2011/0306581 | A1 | 12/2011 | Rapoport et al. |

FOREIGN PATENT DOCUMENTS

| | | |
|---|---|---|
| WO | WO 1997/008315 A1 | 3/1997 |

OTHER PUBLICATIONS

Nikmararn, Nooshin et al, “Emulsion bases systems for fabrication of electrspun nanofibers: food, pharmaceutical and biomedical applications.” RSC Adv. (2017) 7 p. 28951-28964.*

Brecki et al., “Einstein's Viscosity Equation for Nanolubricated Friction”, Langmuir, Oct. 30, 2018, 34(43): 12968-12973.

Fischer Scientific catalog page for Catalog No. AC386790100, Perfluorooctyl bromide, 99%, Thermo Scientific Chemicals, downloaded May 1, 2023.

Freire et al., “Solubility of water in fluorocarbons: Experimental and COSMO-RS prediction results”, J. Chem. Thermodynamics, Feb. 2010, 42(2): 213-219.

International Preliminary Report on Patentability for PCT International Patent Application No. PCT/US2018/056608 mailed Feb. 21, 2019, 12 pages.

International Search Report and Written Opinion for PCT International Patent Application No. PCT/US2018/056608 mailed Feb. 21, 2019, 12 pages.

Kweon et al., “Physical properties of silk fibroin/chitosan blend films”, J. Appl. Polymer Sci., Mar. 2, 2001, 80(7): 928-934.

Sigma Aldrich catalog page for Item No. 442747-U, Perfluorotributylamine (PFTBA), downloaded Mar. 15, 2022.

Tawfic et al., “Liquid Ventilation”, Oman Medical Journal, Jan. 2011, 26(1): 4-9.

Wenk et al., “Silk fibroin as a vehicle for drug delivery applications”, Journal of Controlled Release, Mar. 10, 2011, vol. 150, Issue 2, pp. 128-141.

Wenk et al., “The use of sulfonated silk fibroin derivatives to control binding, delivery and potency of FGF-2 in tissue regeneration”, Biomaterials, 2010, vol. 31, Issue 6, pp. 1403-1413.

* cited by examiner

*Primary Examiner* — Fred H Reynolds

(74) *Attorney, Agent, or Firm* — Dawn-Marie Bey; Bey & Cotropia PLLC

(57) ABSTRACT

Provided are compositions comprising silk fibroin, perfluorocarbon (PFC), and surfactant, and methods of use thereof. The compositions can further comprise a drug, an antibody, or a vaccine. Compositions of the invention are useful in the treatment of certain lung diseases and conditions, including in particular those characterized by surfactant deficiency. Compositions of the invention are particularly useful in the treatment of respiratory distress syndrome (RDS). Also provided are methods for making the compositions, and kits comprising components of the compositions.

2 Claims, 1 Drawing Sheet

Specification includes a Sequence Listing.

SILK FIBROIN-CONTAINING COMPOSITION AND METHODS OF USE THEREOF

RELATED APPLICATIONS

This application is a continuation of U.S. patent application Ser. No. 16/757,195, filed Apr. 17, 2020, which is a U.S. national stage of PCT/US2018/056608, filed Oct. 19, 2018, and which claims benefit of priority to U.S. Provisional Patent Application No. 62/574,993, filed Oct. 20, 2017, the entire contents of each which are incorporated herein by reference.

SEQUENCE LISTING

The instant application contains a Sequence Listing which has been submitted electronically in XML format and is hereby incorporated by reference in its entirety. Said XML file, created on May 2, 2024, is named 754601_GUS-021CON_ST26.xml and is 1,895 bytes in size.

BACKGROUND

Liquid silk is produced by a variety of insects and spiders. The best characterized silks are cocoon silk from the domesticated silkworm *Bombyx mori. Bombyx mori* silk is composed of a core protein, silk fibroin, and a glue-like coating consisting of a nonfilamentous protein, sericin. The core protein of *Bombyx mori* silk is made from two structural proteins, fibroin heavy chain (~325 kDa) and light chain (~25 kDa). The fibroin heavy chain protein consists of layers of antiparallel beta sheets, and its primary structure mainly consists of the recurrent hydrophobic amino acid sequence Gly-Ser-Gly-Ala-Gly-Ala (GSGAGA) (SEQ ID NO:1). Silk fibroin is a natural or synthetic polymer used in textile production, medical sutures, and more recently as a scaffold for tissue regeneration and other medical applications.

Because of their characteristics, perfluorochemicals have been proposed for use as perfusates for organs, as blood substitutes, and as liquids for liquid lavaging or liquid ventilation of the lungs. Perfluorocarbons (PFCs) are chemically inert materials that are known to enable oxygen transport in mammalian systems. For example, rats have been shown to survive total immersion in a liquid perfluorochemical saturated with oxygen. The high solubility of oxygen in most perfluorochemicals enables the rat to "breathe" the perfluorochemical. This process, and its variants, are commonly referred to as liquid ventilation. In one form of liquid ventilation, known as perfluorochemical assisted gas exchange (PAGE), a pure fluorochemical liquid is instilled into the lungs of an animal in an amount equal to the functional residual capacity of the lungs. The animal then is connected to a mechanical ventilator which delivers tidal volumes of a breathable gas to the lungs. However, the PAGE technique is extremely limited with respect to the ability to deliver drugs to the lungs. Because perfluorochemicals are both hydrophobic and lipophobic, very few medicaments other than halocarbon anesthetics may be delivered to the lungs using such liquid breathing techniques.

Surfactant therapy has substantially improved the survival of premature infants with respiratory distress syndrome (RDS), which results from a deficiency of pulmonary surfactant. However, exogenous surfactant is not uniformly effective in treating preterm infants with RDS because the surfactant fails to reach atelectatic alveoli. Perfluorocarbons have been shown to be effective in recruiting atelectatic areas but do not replace impaired endogenous surfactant.

SUMMARY

It has now been discovered by the present inventor that silk fibroin, PFC, and lung surfactant can be combined to form an aqueous emulsion, and that such preparation can (i) prolong the effect of lung surfactant, (ii) lead to a substantially more rapid improvement of oxygenation compared to lung surfactant alone, and (iii) lead to a more homogenous distribution of surfactant. Importantly, such preparation also provides substantial improvement in lung volumes, lung compliance, oxygenation, and ventilation compared to surfactant or PFC alone. This mixture will improve delivery to lung of both surfactant and PFC, and it will find use in the treatment of various lung diseases and conditions, notably including RDS in preterm infants. This mixture may also be used as lung lavage in other infant disease conditions such as MAS (meconium aspiration syndrome) and/or pneumonia and to improve lung function.

An aspect of the invention is a composition comprising silk fibroin and a perfluorocarbon. In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

An aspect of the invention is a composition comprising silk fibroin and a surfactant. In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

An aspect of the invention is a composition comprising silk fibroin, a perfluorocarbon, and a surfactant. In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof. In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, any one of the foregoing compositions further comprises a drug, enzyme, antibody, or vaccine.

An aspect of the invention is a method of making any one of the foregoing compositions.

An aspect of the invention is a method of treating a lung disease or lung condition, comprising administering a therapeutically effective amount of any one of the aforementioned compositions to an airway of a subject in need thereof. In certain embodiments, the subject is a human. In certain embodiments, the subject is a preterm infant. In certain embodiments, the subject is an infant. In certain embodiments, the lung disease or lung condition is selected from the group consisting of respiratory failure, surfactant deficiency, respiratory distress syndrome (RDS), adult respiratory distress syndrome (ARDS), meconium aspiration syndrome, hyaline membrane disease, pneumonia, cystic fibrosis, idiopathic pulmonary fibrosis, atelectasis, and any combination thereof. In certain embodiments, the lung disease or lung condition is respiratory distress syndrome (RDS). In certain embodiments, the administering comprises liquid ventilation. In certain embodiments, the administering comprises lung lavage, e.g., bronchoalveolar lavage (BAL).

An aspect of the invention is a kit comprising components of any one of the aforementioned compositions.

DETAILED DESCRIPTION

Figure 1A:
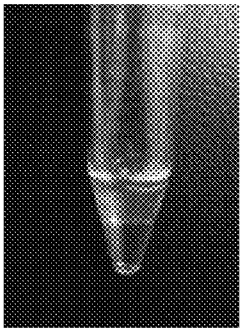
FIG. 1A is a photographic image depicting an aqueous mixture of silk fibroin and PFC (perfluorooctylbromide).

Compositions of the invention include aqueous mixtures of silk fibroin and (a) perfluorocarbon, (b) surfactant, or (c) both perfluorocarbon and surfactant. Each of the components silk fibroin, perfluorocarbon, and surfactant, is deemed to be an active agent. As disclosed herein, in certain embodiments the compositions or mixtures of the invention can further comprise one or more additional agents, including other active pharmaceutical ingredients (APIs). Also as disclosed herein, the compositions of the invention are believed to be useful in the treatment of certain lung diseases and lung conditions, including ARDS.

The silk fibroin component is believed to facilitate the delivery, and therefore enhance the efficacy, of each component with which it is combined in accordance with the compositions of the invention. In fact, it is believed that the combination of silk fibroin, perfluorocarbon, and surfactant exhibits synergistic biological properties over any pair of these three components.

In certain embodiments, the aqueous mixtures are dispersions. In certain embodiments, the aqueous mixtures are emulsions. In certain embodiments, the aqueous mixtures are microemulsions. As will be discussed below, the various components can be combined in various relative amounts or ratios.

As used herein, a "silk fibroin" or "fibroin" refers to natural or recombinant silk fibroin. In certain embodiments, the silk fibroin is derived from the domesticated *Bombyx mori* silkworm. In certain embodiments, "silk fibroin" refers to an aqueous solution containing natural or recombinant silk fibroin protein. See, for example, U.S. Pat. No. 7,635,755, International Patent Application Publication No. WO 97/08315, and U.S. Pat. No. 5,245,012, the entire contents of which are incorporated herein by reference.

Silk is a well described natural fiber produced by the silkworm, *Bombyx mori*, which has been used traditionally in the form of threads in textiles for thousands of years. This silk contains a fibrous protein termed fibroin (both heavy and light chains) that form the thread core, and glue-like proteins termed sericin that surround the fibroin fibers to cement them together. The fibroin is a highly insoluble protein containing up to 90% the amino acids glycine, alanine and serine leading to β-pleated sheet formation in the fibers (Asakura, et al., *Encyclopedia of Agricultural Science*, Arntzen, C. J., Ritter, E. M. Eds.; Academic Press: New York, N.Y., 1994; Vol. 4, pp 1-11).

Silk fibroin has been proposed as a vehicle for drug delivery. See, for example, Wenk et al. *Biomaterials* 31: 1403-13 (2010), and Wenk et al. *J Control Release* 150: 128-41 (2011), the entire contents of which are incorporated herein by reference. Silk fibroin has unique self-assembly process (driving force: hydrophobicity and electrostatic interactions), and it acts like a cocoon for biological matter. Cells show normal growth and proliferation in the presence of silk fibroin. A common and straightforward way to incorporate drugs into the fabrication of silk fibroin delivery system is by dissolving or mixing them directly into silk fibroin solution. Addition of enzymes or antibodies or vaccines to liquid silk solution (the self-assembly process) preserves the biological function of these compounds.

In certain embodiments, the silk fibroin is provided as a commercial product, for example, silk fibroin 50 mg/mL in aqueous solution (Sigma-Aldrich).

As used herein, a "perfluorocarbon" or "PFC" refers to a hydrocarbon, or optionally a substituted hydrocarbon, in which all C—H bonds have been replaced by C—F bonds. Perfluorocarbons include perfluoroalkanes, perfluoroalkenes, perfluoroalkynes, and perfluoroaromatic compounds. In certain embodiments, a "perfluorocarbon" refers to a perfluoroalkane. The alkane portion can be unbranched, branched, or cyclical. There are five perfluoroalkane gases: tetrafluoromethane (bp −128° C.), hexafluoroethane (bp −78.2° C.), octafluoropropane (bp −36.5° C.), perfluoro-n-butane (bp −2.2° C.), and perfluoro-iso-butane (bp −1° C.). Nearly all other fluoroalkanes are liquids.

PFC liquids have low surface tension and at atmospheric pressure, large amounts of oxygen and carbon dioxide dissolve in them. For example, PFC carries 20 times more oxygen than saline/water and twice that of blood. The $O_2$ diffusion rate from PFC-filled alveoli to the alveolar capillaries is quite high. Clear, colorless, odorless, non-conducting, and non-flammable, PFCs are insoluble in water and only sparingly soluble in lipid. PFCs are not metabolized in body tissues.

In certain embodiments, a perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof. In certain embodiments, a perfluorocarbon is perfluorooctylbromide.

A perfluorocarbon may be presented in a gas or liquid form. Liquid forms may include a water-in-perfluorocarbon stable liquid dispersion or a perfluorocarbon-in-water micro-emulsion. Homogenous water-in-perfluorochemical stable liquid dispersions are disclosed in U.S. Pat. No. 5,770,585, the entire content of which is incorporated herein by reference.

In certain embodiments, a perfluorocarbon is provided as a commercial product, for example, LiquiVent® (perfluorooctylbromide; perflubron; Origen Biomedical, Austin, TX).

As used herein, a "surfactant" refers to a compound that lowers the surface tension between two liquids or between a liquid and a solid. In certain embodiments, a surfactant is a pulmonary surfactant.

Pulmonary surfactant is a surface-active phospholipoprotein complex formed by type II alveolar cells of the lung. The proteins and lipids that make up the surfactant have both hydrophilic and hydrophobic regions. By adsorbing to the air-water interface of alveoli, with hydrophilic head groups in the water and the hydrophobic tails facing towards the air, the main lipid component of surfactant, dipalmitoylphosphatidylcholine (DPPC), reduces surface tension. Pulmonary surfactant increases pulmonary compliance and facilitates recruitment of collapsed (atelectatic) airways. Most preterm infants are surfactant-deficient at birth and as a result have respiratory problems, including respiratory distress syndrome (RDS). RDS is a major cause of premature infant morbidity and mortality.

Pulmonary surfactants generally include synthetic pulmonary surfactants and animal-derived pulmonary surfactants. Both synthetic pulmonary surfactants and animal-derived pulmonary surfactants are useful in the invention.

Synthetic pulmonary surfactants include, without limitation, colfosceril palmitate (Exosurf), a mixture of dipalmitoylphosphatidylcholine (DPPC) with hexadecanol and tyloxapol; pumactant, a mixture of DPPC and phosphatidylglycerol (PG); KL-4, a mixture of DPPC, palmitoyl-oleoyl phosphatidylglycerol, and palmitic acid, combined with a 21 amino acid synthetic peptide that mimics the structural characteristics of surfactant protein B (SP-B); venticute, a mixture of DPPC, PG, palmitic acid, and recombinant surfactant protein C (SP-C); and lucinactant (Surfaxin), a mixture of KL4 acetate, 1,2-dipalmitoyl-sn-glycero-3-phosphocholine, 1-palmitoyl-2-oleoyl-sn-glycero-3-phosphoglycerol (as the sodium salt), and palmitic acid. PG consists of an L-glycerol 3-phosphate backbone ester-bonded to either saturated or unsaturated fatty acids on carbons 1 and 2.

Animal-derived pulmonary surfactants include, without limitation, beractant, Alveofact (extracted from cow lung lavage fluid, manufactured by Boehringer Ingelheim), Survanta (extracted from minced cow lung with additional DPPC, palmitic acid and tripalmitin, manufactured by Abbvie), Beraksurf (extracted from minced cow lung with additional DPPC, palmitic acid and tripalmitin manufactured by Tekzima), calfactant (Infasurf, extracted from calf lung lavage), and proactant alfa (Curosurf®, extracted from material derived from minced pig lung).

In certain embodiments, the surfactant is provided as a commercial product, for example, calfactant (Infasurf®).

As used herein, a "lung disease" refers to any congenital or acquired lung disease characterized by impairment of gas exchange. Lung diseases include, without limitation, surfactant deficiency, respiratory distress syndrome (RDS), adult respiratory distress syndrome (ARDS), meconium aspiration syndrome, pneumonia, cystic fibrosis, idiopathic pulmonary fibrosis, bronchitis, emphysema, and lung cancer.

As used herein, a "lung condition" refers to any congenital or acquired lung condition, other than a lung disease, characterized by impairment of gas exchange. Lung conditions include, without limitation, atelectasis.

As used herein, a "preterm infant" refers to an infant born at less than 32 weeks gestational age.

As used herein, an "infant" refers to a human baby less than one year old. In certain embodiments, an infant is a neonate or newborn.

As used herein, "respiratory failure" refers to compromise of lung gas exchange from any cause, characterized by diminished $PaO_2$ and/or increased $PaCO_2$ (without treatment) compared to normal values. In certain embodiments, respiratory failure is characterized by $PaO_2$ (without treatment) of less than or equal to 50 mm Hg. In certain embodiments, respiratory failure is sufficiently severe as to require supplemental oxygen. In certain embodiments, respiratory failure is sufficiently severe as to require mechanical ventilation. Respiratory failure can be acute or chronic.

As used herein, "surfactant deficiency" refers to any congenital or acquired deficiency of pulmonary surfactant. In certain embodiments, surfactant deficiency is accompanied by respiratory failure. Surfactant deficiency can be natural or it can be experimentally induced.

As used herein, the terms "respiratory distress syndrome" or "RDS" refer to a breathing disorder that affects newborns, especially preterm infants. It is believed to be caused by pulmonary surfactant deficiency due at least in part to immaturity of the type II alveolar cells which are the principal source of pulmonary surfactant. This syndrome is also variously known as infant respiratory distress syndrome (IRDS), neonatal respiratory distress syndrome, surfactant deficiency disorder, and hyaline membrane disease.

Acute respiratory distress syndrome (ARDS) is life-threatening condition that can develop principally in adults and is characterized by inflammation of and abnormal accumulation of fluid in alveoli of the lung. ARDS may be seen in the setting of a critical illness, e.g., severe pulmonary (pneumonia) or systemic infection (sepsis), following trauma, multiple blood transfusions, severe burns, severe pancreatitis, near-drowning, drug reactions, or inhalation injuries. ARDS is characterized by: lung injury of acute onset, within 1 week of an apparent clinical insult and with progression of respiratory symptoms; bilateral opacities on chest imaging (chest X-ray or CT) not explained by other lung pathology; respiratory failure not explained by heart failure or volume overload; and decreased $PaO_2/FiO_2$ ratio.

As used herein, "liquid ventilation" refers to a technique of mechanical ventilation in which the lungs are insufflated with an oxygenated perfluorochemical liquid rather than an oxygen-containing gas mixture. For a review, see Tawfic et al., *Oman Med J* 26: (1): 4-9 (2011).

As used herein, "total liquid ventilation" refers to a type of liquid ventilation in which the lungs are filled with PFC to a volume equivalent to the functional residual capacity, approximately 30 mL/kg, and a liquid ventilator is used to generate tidal breathing with perfluorocarbon.

As used herein, "partial liquid ventilation" refers to a type of liquid ventilation in which tracheal instillation of PFC liquid is used in combination with conventional gas mechanical ventilation.

Compositions

An aspect of the invention is a composition comprising silk fibroin and a perfluorocarbon. In certain embodiments, the silk fibroin is provided as an aqueous solution. In certain embodiments, the perfluorocarbon is provided as an aqueous solution. In certain embodiments, the composition is an aqueous solution comprising silk fibroin and a perfluorocarbon. In certain embodiments, the composition is an aqueous dispersion comprising silk fibroin and a perfluorocarbon. In certain embodiments, the composition is an aqueous emulsion comprising silk fibroin and a perfluorocarbon.

In certain embodiments, the composition further comprises a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide (1-Bromoperfluorooctane), e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the composition further comprises another active pharmaceutical agent (API). In certain embodiments, said other API is a drug, enzyme, antibody, or vaccine. In certain embodiments, said other API is a steroid, a diuretic, or deoxyribonuclease (DNAse) enzyme.

Exemplary steroids include, without limitation, methylprednisone, beclomethasone, dexamethasone, budesonide, flunisolide, fluticasone, and hydrocortisone.

Exemplary diuretics include, without limitation, furosemide, bumetanide, and amiloride.

A further aspect of the invention is a composition comprising silk fibroin and a surfactant. In certain embodiments, the silk fibroin is provided as an aqueous solution. In certain embodiments, the surfactant is provided as an aqueous solution. In certain embodiments, the composition is an aqueous solution comprising silk fibroin and a surfactant. In certain embodiments, the composition is an aqueous dispersion comprising silk fibroin and a surfactant. In certain embodiments, the composition is an aqueous emulsion comprising silk fibroin and a surfactant.

In certain embodiments, the composition further comprises a pharmaceutically acceptable carrier, such as is described elsewhere herein.

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v).

In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the composition further comprises another active pharmaceutical agent (API). In certain embodiments, said other API is a drug, enzyme, antibody, or vaccine. In certain embodiments, said other API is a steroid, diuretic, or deoxyribonuclease (DNAse) enzyme.

A yet further aspect of the invention is a composition comprising silk fibroin, a perfluorocarbon, and a surfactant. In certain embodiments, the silk fibroin is provided as an aqueous solution. In certain embodiments, the perfluorocarbon is provided as an aqueous solution. In certain embodiments, the surfactant is provided as an aqueous solution. In certain embodiments, the composition is an aqueous solution comprising silk fibroin, a perfluorocarbon, and a surfactant. In certain embodiments, the composition is an aqueous dispersion comprising silk fibroin, a perfluorocarbon, and a surfactant. In certain embodiments, the composition is an aqueous emulsion comprising silk fibroin, a perfluorocarbon, and a surfactant.

In certain embodiments, the composition further comprises a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide (1-Bromoperfluorooctane), e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v).

In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the composition further comprises another active pharmaceutical agent (API). In certain embodiments, said other API is a drug, enzyme, antibody, or vaccine. In certain embodiments, said other API is a steroid, diuretic, or deoxyribonuclease (DNAse) enzyme.

Methods of Making

An aspect of the invention is a method of making a composition comprising silk fibroin and a perfluorocarbon. The method includes the step of placing the silk fibroin and the perfluorocarbon in an aqueous medium. In certain embodiments, the method further includes the step of mixing the silk fibroin and the perfluorocarbon in the aqueous medium. The mixing can be accomplished by any suitable means, including, without limitation, stirring, rocking, shaking, and vortexing.

In certain embodiments, the silk fibroin is provided as an aqueous solution. In certain embodiments, the perfluorocarbon is provided as an aqueous solution. In certain embodiments, the composition is an aqueous solution comprising silk fibroin and a perfluorocarbon. In certain embodiments, the composition is an aqueous dispersion comprising silk fibroin and a perfluorocarbon. In certain embodiments, the composition is an aqueous emulsion comprising silk fibroin and a perfluorocarbon.

In certain embodiments, the method comprises placing the silk fibroin and the perfluorocarbon in a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide, e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the method further comprises contacting the silk fibroin and the perfluorocarbon with another active pharmaceutical agent (API). In certain embodiments, said other API is a drug, enzyme, antibody, or vaccine. In certain embodiments, said other API is a steroid, diuretic, or deoxyribonuclease (DNAse) enzyme.

An aspect of the invention is a method of making a composition comprising silk fibroin and a surfactant. The method includes the step of placing the silk fibroin and the surfactant in an aqueous medium. In certain embodiments, the method further includes the step of mixing the silk fibroin and the surfactant in the aqueous medium. The mixing can be accomplished by any suitable means, including, without limitation, stirring, rocking, shaking, and vortexing.

In certain embodiments, the silk fibroin is provided as an aqueous solution. In certain embodiments, the surfactant is provided as an aqueous solution. In certain embodiments, the composition is an aqueous solution comprising silk fibroin and a surfactant. In certain embodiments, the composition is an aqueous dispersion comprising silk fibroin and a surfactant. In certain embodiments, the composition is an aqueous emulsion comprising silk fibroin and a surfactant.

In certain embodiments, the method comprises placing the silk fibroin and the surfactant in a pharmaceutically acceptable carrier, such as is described elsewhere herein.

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v).

In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the method further comprises contacting the silk fibroin and the surfactant with another active pharmaceutical agent (API). In certain embodiments, said other API is a drug, enzyme, antibody, or vaccine. In certain embodiments, said other API is a steroid, diuretic, or deoxyribonuclease (DNAse) enzyme.

A yet further aspect of the invention is a method of making a composition comprising silk fibroin, a perfluorocarbon, and a surfactant. The method includes the step of placing the silk fibroin, the perfluorocarbon, and the surfactant in an aqueous medium. In certain embodiments, the method further includes the step of mixing the silk fibroin, the perfluorocarbon, and the surfactant in the aqueous medium. The mixing can be accomplished by any suitable means, including, without limitation, stirring, rocking, shaking, and vortexing.

In certain embodiments, the silk fibroin is provided as an aqueous solution. In certain embodiments, the perfluorocarbon is provided as an aqueous solution. In certain embodiments, the surfactant is provided as an aqueous solution. In certain embodiments, the composition is an aqueous solution comprising silk fibroin, a perfluorocarbon, and a surfactant. In certain embodiments, the composition is an aqueous dispersion comprising silk fibroin, a perfluorocarbon, and a surfactant. In certain embodiments, the composition is an aqueous emulsion comprising silk fibroin, a perfluorocarbon, and a surfactant.

In certain embodiments, the method comprises placing the silk fibroin, perfluorocarbon, and surfactant in a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide (1-Bromoperfluorooctane), e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v).

In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the method further comprises the step of contacting the silk fibroin, perfluorocarbon, and surfactant with an active pharmaceutical agent (API). In certain embodiments, said other API is a drug, enzyme, antibody, or vaccine. In certain embodiments, said other API is a steroid, diuretic, or deoxyribonuclease (DNAse) enzyme.

Methods of Using

An aspect of the invention is a method of treating a lung disease or lung condition, comprising administering a therapeutically effective amount of a composition comprising silk fibroin and a perfluorocarbon to an airway of a subject in need thereof.

As used herein, the terms "treat" and "treating" refer to reducing or ameliorating at least one sign or symptom of a disease or condition of a subject having said disease or condition. In certain embodiments, the terms "treat" and "treating" encompass curing a disease or condition of a subject having said disease or condition.

As used herein, the term "therapeutically effective amount" refers to an amount sufficient to achieve a desired therapeutic result in a subject. For example, a therapeutically effective amount can refers to an amount sufficient to reduce or ameliorate at least one sign or symptom of a disease or condition of a subject having said disease or condition.

As used herein, an "airway" refers to any conducting or gas-exchanging anatomical structure. In certain embodiments, an airway is any one or combination of trachea, bronchi, bronchioles, and alveoli.

As used herein, a "subject" refers to a living animal. In certain embodiments, a subject is a mammal. In certain embodiments, a subject is a mammal selected from the group consisting of mice, rats, hamsters, guinea pigs, rabbits, goats, sheep, cats, dogs, pigs, horses, cows, and non-human primates. In certain embodiments, a subject is a human. In some embodiments, a subject is a preterm infant. In some embodiments, a subject is an infant. In some embodiments, a subject is a human 1 to 18 years of age. In some embodiments, a subject is an adult human.

In certain embodiments, the silk fibroin is provided as an aqueous solution. In certain embodiments, the perfluorocarbon is provided as an aqueous solution. In certain embodiments, the composition is an aqueous solution comprising silk fibroin and a perfluorocarbon. In certain embodiments, the composition is an aqueous dispersion comprising silk fibroin and a perfluorocarbon. In certain embodiments, the composition is an aqueous emulsion comprising silk fibroin and a perfluorocarbon.

In certain embodiments, the composition further comprises a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide (1-Bromoperfluorooctane), e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the composition further comprises another active pharmaceutical agent (API). In certain embodiments, said other API is a drug, enzyme, antibody, or vaccine. In certain embodiments, said other API is a steroid, diuretic, or deoxyribonuclease (DNAse) enzyme.

In certain embodiments, the subject is a preterm infant.

In certain embodiments, the subject is an infant.

In certain embodiments, the subject is an adult human.

In certain embodiments, the lung disease or lung condition is selected from the group consisting of respiratory failure, surfactant deficiency, respiratory distress syndrome (RDS), adult respiratory distress syndrome (ARDS), meconium aspiration syndrome, hyaline membrane disease, pneumonia, cystic fibrosis, idiopathic pulmonary fibrosis, atelectasis, and any combination thereof.

In certain embodiments, the lung disease or lung condition is respiratory distress syndrome (RDS).

In certain embodiments, the administering comprises liquid ventilation.

In certain embodiments, the liquid ventilation is total liquid ventilation.

In certain embodiments, the liquid ventilation is partial liquid ventilation.

A further aspect of the invention is a method of treating a lung disease or lung condition, comprising administering a therapeutically effective amount of a composition comprising silk fibroin and a surfactant to an airway of a subject in need thereof.

In certain embodiments, the silk fibroin is provided as an aqueous solution. In certain embodiments, the surfactant is provided as an aqueous solution. In certain embodiments, the composition is an aqueous solution comprising silk fibroin and a surfactant. In certain embodiments, the composition is an aqueous dispersion comprising silk fibroin and a surfactant. In certain embodiments, the composition is an aqueous emulsion comprising silk fibroin and a surfactant.

In certain embodiments, the composition further comprises a pharmaceutically acceptable carrier, such as is described elsewhere herein.

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v). In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the composition further comprises another active pharmaceutical agent (API). In certain embodiments, said other API is a drug, enzyme, antibody, or vaccine. In certain embodiments, said other API is a steroid, diuretic, or deoxyribonuclease (DNAse) enzyme.

In certain embodiments, the subject is a preterm infant.

In certain embodiments, the subject is an infant.

In certain embodiments, the subject is an adult human.

In certain embodiments, the lung disease or lung condition is selected from the group consisting of respiratory failure, surfactant deficiency, respiratory distress syndrome (RDS), adult respiratory distress syndrome (ARDS), meconium aspiration syndrome, hyaline membrane disease, pneumonia, cystic fibrosis, idiopathic pulmonary fibrosis, atelectasis, and any combination thereof.

In certain embodiments, the lung disease or lung condition is respiratory distress syndrome (RDS).

In certain embodiments, the administering comprises liquid ventilation.

In certain embodiments, the liquid ventilation is total liquid ventilation.

In certain embodiments, the liquid ventilation is partial liquid ventilation.

A yet further aspect of the invention is a method of treating a lung disease or lung condition, comprising administering a therapeutically effective amount of a composition comprising silk fibroin, a perfluorocarbon, and a surfactant to an airway of a subject in need thereof.

In certain embodiments, the silk fibroin is provided as an aqueous solution. In certain embodiments, the perfluorocarbon is provided as an aqueous solution. In certain embodiments, the surfactant is provided as an aqueous solution. In certain embodiments, the composition is an aqueous solution comprising silk fibroin, a perfluorocarbon, and a surfactant. In certain embodiments, the composition is an aqueous dispersion comprising silk fibroin, a perfluorocarbon, and a surfactant. In certain embodiments, the composition is an aqueous emulsion comprising silk fibroin, a perfluorocarbon, and a surfactant.

In certain embodiments, the composition further comprises a pharmaceutically acceptable carrier, such as is described elsewhere herein.

In certain embodiments, the perfluorocarbon is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and any combination thereof.

In certain embodiments, the perfluorocarbon is perfluorooctylbromide (1-Bromoperfluorooctane), e.g., perflubron.

In certain embodiments, the ratio of silk fibroin to perfluorocarbon is about 1:4 to 1:1 (v/v). For example, in certain embodiments, the ratio of silk fibroin to perfluorocarbon is about 1:4 (v/v). In certain embodiments, the ratio of silk fibroin to perfluorocarbon is about 1:3 (v/v). In certain embodiments, the ratio of silk fibroin to perfluorocarbon is about 1:2 (v/v). In certain embodiments, the ratio of silk fibroin to perfluorocarbon is about 1:1 (v/v).

In certain embodiments, the ratio of silk fibroin to perfluorocarbon is about 1:4 to 1:2 (v/v).

In certain embodiments, the ratio of silk fibroin to perfluorocarbon is about 1:4 to 1:3 (v/v).

In certain embodiments, the ratio of silk fibroin to perfluorocarbon is about 1:3 to 1:1 (v/v).

In certain embodiments, the ratio of silk fibroin to perfluorocarbon is about 1:3 to 1:2 (v/v).

In certain embodiments, the ratio of silk fibroin to perfluorocarbon is about 1:2 to 1:1 (v/v).

In certain embodiments, the surfactant is a pulmonary surfactant.

In certain embodiments, the surfactant is selected from the group consisting of egg yolk phospholipid, polyalkyleneoxides, 1,2-dialkylglycero-3-phosphoryl cholines, 1,3-dialkylglycero-2-phosphoryl cholines, perfluorinated polyoxyethylenes, and any combination thereof. In certain embodiments, the surfactant is not a perfluorocarbon.

In certain embodiments, the surfactant is calfactant.

In certain embodiments, the ratio of silk fibroin to surfactant is about 1:6 to 1:2 (v/v). For example, in certain embodiments, the ratio of silk fibroin to surfactant is about 1:6 to 1:2.5 (v/v). In certain embodiments, the ratio of silk fibroin to surfactant is about 1:6 (v/v). In certain embodiments, the ratio of silk fibroin to surfactant is about 1:5 (v/v). In certain embodiments, the ratio of silk fibroin to surfactant is about 1:4 (v/v). In certain embodiments, the ratio of silk fibroin to surfactant is about 1:3 (v/v). In certain embodiments, the ratio of silk fibroin to surfactant is about 1:2.5 (v/v). In certain embodiments, the ratio of silk fibroin to surfactant is about 1:2 (v/v).

In certain embodiments, the ratio of silk fibroin to surfactant is about 1:6 to 1:3 (v/v).

In certain embodiments, the ratio of silk fibroin to surfactant is about 1:6 to 1:4 (v/v).

In certain embodiments, the ratio of silk fibroin to surfactant is about 1:6 to 1:5 (v/v).

In certain embodiments, the ratio of silk fibroin to surfactant is about 1:5 to 1:2 (v/v).

In certain embodiments, the ratio of silk fibroin to surfactant is about 1:5 to 1:2.5 (v/v).

In certain embodiments, the ratio of silk fibroin to surfactant is about 1:5 to 1:3 (v/v).

In certain embodiments, the ratio of silk fibroin to surfactant is about 1:5 to 1:4 (v/v).

In certain embodiments, the ratio of silk fibroin to surfactant is about 1:4 to 1:2 (v/v).

In certain embodiments, the ratio of silk fibroin to surfactant is about 1:4 to 1:2.5 (v/v).

In certain embodiments, the ratio of silk fibroin to surfactant is about 1:4 to 1:3 (v/v).

In certain embodiments, the ratio of silk fibroin to surfactant is about 1:3 to 1:2 (v/v).

In certain embodiments, the ratio of silk fibroin to surfactant is about 1:3 to 1:2.5 (v/v).

In certain embodiments, the composition further comprises another active pharmaceutical agent (API). In certain embodiments, said other API is a drug, enzyme, antibody, or vaccine. In certain embodiments, said other API is a steroid, diuretic, or deoxyribonuclease (DNAse) enzyme.

In certain embodiments, the subject is a human.

In certain embodiments, the subject is a preterm infant.

In certain embodiments, the subject is an infant.

In certain embodiments, the subject is an adult human.

In certain embodiments, the lung disease or lung condition is selected from the group consisting of respiratory failure, surfactant deficiency, respiratory distress syndrome (RDS), adult respiratory distress syndrome (ARDS), meconium aspiration syndrome, hyaline membrane disease, pneumonia, cystic fibrosis, idiopathic pulmonary fibrosis, atelectasis, and any combination thereof.

In certain embodiments, the lung disease or lung condition is respiratory distress syndrome (RDS).

In certain embodiments, the administering comprises liquid ventilation.

In certain embodiments, the liquid ventilation is total liquid ventilation.

In certain embodiments, the liquid ventilation is partial liquid ventilation.

Formulation and Dosing

Compositions of the invention can be formulated for administration to lung. For example, a composition of the invention can be formulated with a pharmaceutically acceptable carrier, wherein the composition is provided in a therapeutically effective amount within a volume suitable for administration to an airway of a subject to be treated.

As used herein, a “pharmaceutically acceptable carrier” refers to a biologically compatible aqueous fluid, e.g., water, normal saline, Ringer’s solution, solution buffered to physiologic pH (pH 6.8-7.4).

The pharmaceutically acceptable carrier can optionally include any one or more of salts, buffering agents, osmotically active agents, preservatives, and coloring agents, such as are well known in the pharmaceutical arts. See, e.g., Remington’s *The Science and Practice of Pharmacy*, Lloyd V. Allen, Jr, editor, Philadelphia, PA: Pharmaceutical Press. 2012.

For use in the lung, a suitable amount (volume) of composition of the invention so formulated can be instilled into an airway of the lung, e.g., via an endotracheal tube. Dosing may involve any one or combination of (i) lavage, (ii) partial liquid ventilation, and (iii) total liquid ventilation.

Administration can be accomplished in a single dose or in multiple (i.e., two or more) doses. When the administration is accomplished in multiple doses, each dose can be the same, or at least one dose can differ from another dose.

In certain embodiments, dosing can be based on corresponding surfactant alone.

In certain embodiments, dosing can be based on corresponding PFC alone.

In certain embodiments, the composition is administered once daily, twice daily, three times daily, four times daily, or more. In certain embodiments, the composition is administered every other day, every third day, every fourth day, every fifth day, every sixth day, or every seventh day.

Generally, the administering physician or medical professional will be able to assess and adjust the dose and frequency of dosing based on such parameters as body weight, lung volumes, age, general medical condition, other medical conditions, and laboratory values such as $O_2$ saturation, arterial blood gases (ABGs), and radiographic examination of the lungs.

Kits

An aspect of the invention is a kit comprising silk fibroin in a first container and a perfluorocarbon in a second container. The kit may be conveniently presented with the components packaged together, for example in a box, tray, or foil pouch. The component silk fibroin and perfluorocarbon can be combined by an end user to make a composition in accordance with the invention.

An aspect of the invention is a kit comprising silk fibroin in a first container and a surfactant in a second container. The kit may be conveniently presented with the components packaged together, for example in a box, tray, or foil pouch. The component silk fibroin and surfactant can be combined by an end user to make a composition in accordance with the invention.

An aspect of the invention is a kit comprising silk fibroin in a first container, a perfluorocarbon in a second container, and a surfactant in a third container. The kit may be conveniently presented with the components packaged together, for example in a box, tray, or foil pouch. The component silk fibroin, perfluorocarbon, and surfactant can be combined by an end user to make a composition in accordance with the invention.

Each of the foregoing kits can further include written instructions directing an end user how to assemble and/or administer the various components.

Each of the foregoing kits can further include an applicator or other delivery device suitably constructed and arranged for use in administering the various and/or assembled components to a subject in need thereof. For example, in certain embodiments such applicator or delivery device can be a syringe.

The invention may be further understood by reference to the following nonlimiting examples.

EXAMPLES

Materials

Silk fibroin was obtained from Silk lab, Tufts Science and Technology Center, 4 Colby St Biomed Eng Dept., Medford, MA.

PFC was obtained from Origen Biomedical, Austin, TX.

Lung Surfactant called Infasurf was obtained from ONY, Inc. 1576 Sweet Home Road, Amherst, NY 14228.

Figure 1B:
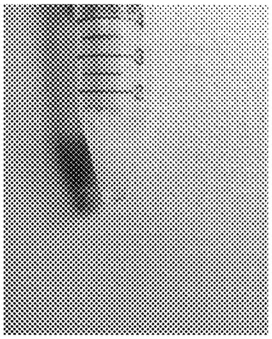
FIG. 1B is a photographic image depicting an aqueous mixture of silk fibroin and surfactant.
Figure 1C:
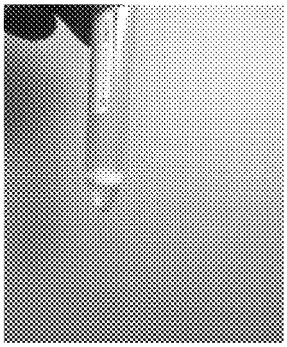
FIG. 1C is a photographic image depicting an aqueous mixture of PFC and surfactant.
Figure 1D:
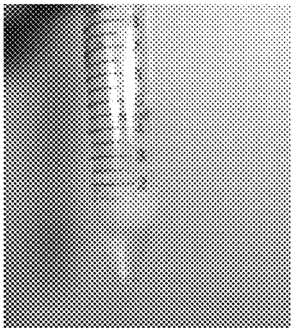
FIG. 1D is a photographic image depicting an aqueous mixture of silk fibroin, surfactant, and PFC prior to vigorous shaking.
Figure 1E:
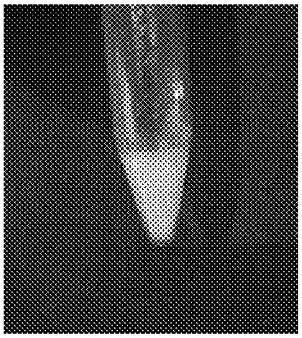
FIG. 1E is a photographic image depicting an aqueous mixture of silk fibroin, surfactant, and PFC after vigorous shaking.

Example 1: Preparation and Characterization of Mixtures of Silk Fibroin, PFC, and Surfactant Aqueous preparations of silk fibroin and perfluorocarbon (PFC); silk fibroin and surfactant; PFC and surfactant; and silk fibroin, PFC, and surfactant were prepared and visually inspected for homogeneity. Selected properties of silk fibroin and PFC are shown in Table 1. Selected properties of silk fibroin and surfactant are shown in Table 2. Representative results are shown in FIGS. 1A-1E.

TABLE 1

Selected properties of silk fibroin and PFC

| Property | Silk Fibroin | PFC |
|---|---|---|
| Drug delivery effect | + | + |
| pH | 6-6.5 | 5-6 |
| $O_2$ permeability | + | +++ |
| Biodegradability | +++ | +++ |
| Biocompatibility | +++ | +++ |
| Water solubility | Yes | No |

TABLE 2

Selected properties of silk fibroin and surfactant

| Property | Silk Fibroin | Surfactant |
|---|---|---|
| Constituents | protein and water | protein and lipid |
| Proteins | Hydrophobic (HMW) Hydrophilic (LMW) | Hydrophobic (BC+) Hydrophilic (A−) |
| Surface Tension | ?? | Low (14-18 Dynes/cm) $H_2O$: 70 Dynes/cm) Lung: 25 Dynes/cm |
| pH | 6-6.5 | 5.0-6.2 |

Silk fibroin and surfactant formed a homogeneous mixture. Surfactant and PFC mixture was nonhomogeneous. Silk fibroin, PFC, and surfactant was homogeneous after vigorous shaking.

Example 2: Silk Fibroin/Perflubron Administration in Surfactant-Deficient Animal Lungs (Rabbit Model)

A New Zealand white rabbit was used to test proof of concept. The animal weighing 1.58 kg anesthetized and after instrumentation, anesthesia was administered continuously as per protocol. The rabbit was intubated orally and ventilated on assist/control mode at 30 breaths/min, 0.4 fraction of inspired oxygen ($FiO_2$), 0.35 sec inspiratory time, 4 cm $H_2O$ positive end expiratory pressure (PEEP), and tidal volume targeted to 7 mL/kg. The lungs were lavaged 4 times with 30 ml/kg of normal (0.9%) saline several times until blood gases were consistent with surfactant deficiency status. After a stabilization period of 30 min on the ventilator, arterial blood gas (ABG) analyses, mean arterial pressure (MAP), and arterial blood pressures were measured prior to administration of liquid fibroin and PFC 1:2 volume ratio (1 mL of silk fibroin to 2 mL of PFC). Oxygen saturations, arterial blood gases, and blood pressure were recorded at the end. Representative results are shown in Table 3.

TABLE 3

Effect of administration of silk fibroin/PFC to surfactant-deficient rabbit.

| Parameter | Before Fibroin/PFC | After Fibroin/PFC |
|---|---|---|
| $O_2$ saturation | 85% | 92% |
| ABG pH/$PaCO_2$/$PaO_2$/ $HCO_3$/base excess | 7.20/65/45/20/−9 | 7.31/55/60/23/−5 |
| BP (mm Hg) | 35/19 | 39/23 |
| MAP (mm Hg) | 24 | 28 |

Administration of mixture of liquid silk fibroin and PFC to surfactant-deficient rabbit resulted in improvement in oxygen saturations and arterial blood gases and stabilization of mean blood pressure. Surfactant has already been shown to be effective in surfactant deficient-lung, strongly suggesting that inclusion of surfactant would only further improve results in this system.

The observed improvement in blood gases and blood pressure after instillation of mixture of silk fibroin and PFC shows possible synergy between two liquids on surfactant-deficient lungs and suggests such mixture will have beneficial effect upon its addition to surfactant and administration to surfactant-deficient lungs.

Example 3. Head-to-Head Comparison of Silk Fibroin/PFC/Surfactant to Individual Components and Pairs of Components Rats, rabbits, or sheep are anesthetized, intubated, ventilated, and made surfactant-deficient in a manner similar to Example 2. Animals are then treated with test agent selected from (i) silk fibroin alone; (ii) PFC alone; (iii) surfactant alone; (iv) vehicle alone; (v) silk fibroin and PFC; (vi) silk fibroin and surfactant; (vii) PFC and surfactant; and/or (viii) silk fibroin, PFC, and surfactant by instillation into the lungs. Arterial blood gas (ABG), mean arterial pressure (MAP), and arterial blood pressures are measured prior to administration of test agent. Oxygen saturations, arterial blood gases, and blood pressures are recorded after administration of test agent. Comparison is made between pre- and post-administration clinical parameters. Results are expected to show that (viii) silk fibroin, PFC, and surfactant is superior to (i) silk fibroin alone; (ii) PFC alone; (iii) surfactant alone; (iv) vehicle alone; (v) silk fibroin and PFC; (vi) silk fibroin and surfactant; and (vii) PFC and surfactant, including synergistic improvement over (v) silk fibroin and PFC; (vi) silk fibroin and surfactant; and/or (vii) PFC and surfactant.

SEQUENCE LISTING

```
Sequence total quantity: 1
SEQ ID NO: 1          moltype = AA  length = 6
FEATURE               Location/Qualifiers
source                1..6
                      mol_type = protein
                      organism = Bombyx mori
SEQUENCE: 1
GSGAGA                                                  6
```

We claim:

1. A composition for treating a surfactant deficiency, the composition comprising an aqueous emulsion including silk fibroin, calfactant and a perfluorocarbon.

2. The composition of claim 1:

wherein the perfluorocarbon is perfluorooctylbromide.

* * * * *